(12) United States Patent
Carneiro et al.

(10) Patent No.: US 10,892,036 B1
(45) Date of Patent: Jan. 12, 2021

(54) SYSTEMS AND METHODS FOR DETERMINING THE IDENTITY OF ALLELES FROM GENOMIC SEQUENCING DATA

(71) Applicant: Verily Life Sciences LLC, Mountain View, CA (US)

(72) Inventors: Mauricio Carneiro, Mountain View, CA (US); Mark DePristo, Palo Alto, CA (US); Ryan Poplin, Sunnyvale, CA (US)

(73) Assignee: Verily Life Sciences LLC, South San Francisco, CA (US)

( * ) Notice: Subject to any disclaimer, the term of this patent is extended or adjusted under 35 U.S.C. 154(b) by 656 days.

(21) Appl. No.: 15/666,924

(22) Filed: Aug. 2, 2017

Related U.S. Application Data (60) Provisional application No. 62/369,809, filed on Aug. 2, 2016.

(51) Int. Cl.
    *G01N 33/48*      (2006.01)
    *G01N 33/50*      (2006.01)
    *G16B 30/00*      (2019.01)

(52) U.S. Cl.
    CPC .................................... *G16B 30/00* (2019.02)

(58) Field of Classification Search
None
See application file for complete search history.

(56) References Cited

U.S. PATENT DOCUMENTS

2014/0322708 A1* 10/2014 Vijg ..................... C12Q 1/6809
    435/6.11

OTHER PUBLICATIONS

Boegel et al., "HLA typing from RNA-Seq sequence reads", Genome medicine 4.12 (2013): 102.
bwa.kit, 2014, retrieved from: https://github.com/lh3/bwa/blob/master/bwakit/Readme.md.
Warren et al., "Derivation of HLA types from shotgun sequence datasets", Genome medicine 4.12 (2012): 95.

\* cited by examiner

*Primary Examiner* — Russell S Negin
(74) *Attorney, Agent, or Firm* — Kilpatrick Townsend & Stockton LLP (57) ABSTRACT

The present invention relates to systems and methods for determining the identity of alleles from genomic sequencing data via pseudoalignments. Particularly, aspects of the present invention are directed to a computer implemented method that includes obtaining a paired-end fragment from a genomic sample, determining a first nucleotide substring from a first end of the paired-end fragment matches a nucleotide substring within an index of nucleotide substrings and alleles, determining a second nucleotide substring from a second end of the paired-end fragment matches another nucleotide substring within the index, determining an intersection between the nucleotide substring and the another nucleotide substring exists, when an allele that contains the nucleotide substring is the same allele that contains the another nucleotide substring; and determining a probability that the paired end fragment is an observation of the allele based on the existence of the intersection.

13 Claims, 6 Drawing Sheets

Specification includes a Sequence Listing.

| Data likelihoods | # of fragments | A*01:01 | A*01:02 | A*01:03 | A*01:04N |
|---|---|---|---|---|---|
| Fragment class 1 | 9 | 1 | 0 | 0 | 0 |
| Fragment class 2 | 1 | 0 | 0 | 1 | 1 |

| Resulting likelihood of allele | | 0.9 | 0 | 0.05 | 0.05 |

SEQUENCE LISTING

<160> NUMBER OF SEQ ID NOS: 25

<210> SEQ ID NO 1
<211> LENGTH: 300
<212> TYPE: DNA
<213> ORGANISM: Homo sapiens

<400> SEQUENCE: 1
caggagcaga ggggtcaggg cgaagtccca gggccccagg cgtggctctc agggtctcag      60
gccccgaagg cggtgtatgg attggggagt cccagccttg gggattcccc aactccgcag     120
tttcttttct ccctctccca acctacgtag ggtccttcat cctggatact cacgacgcgg     180
acccagttct cactcccatt gggtgtcggg tttccagaga agccaatcag tgtcgtcgcg     240
gtcgctgttc taaagtccgc acgcacccac cgggactcag attctcccca gacgccgagg     300

<210> SEQ ID NO 2
<211> LENGTH: 360
<212> TYPE: DNA
<213> ORGANISM: Homo sapiens

<400> SEQUENCE: 2
gggagtccca gccttgggga ttccccaact ccgcagtttc ttttctccct ctcccaacct      60
acgtagggtc cttcatcctg gatactcacg acgcggaccc agttctcact cccattgggt     120
gtcgggtttc agagaagcc aatcagtgtc gtcgcggtcg ctgttctaaa gtccgcacgc      180
acccaccggg actcagattc tccccagacg ccgaggatgg ccgtcatggc gccccgaacc     240
ctcctcctgc tactctcggg ggccctggcc ctgacccaga cctgggcggg tgagtgcggg     300
gtcgggaggg aaaccgcctc tgcggggaga agcaaggggc cctcctggcg ggggcgcagg     360

<210> SEQ ID NO 3
<211> LENGTH: 10
<212> TYPE: DNA
<213> ORGANISM: Homo sapiens

<400> SEQUENCE: 3
caggagcaga                                                             10

<210> SEQ ID NO 4
<211> LENGTH: 10
<212> TYPE: DNA
<213> ORGANISM: Homo sapiens

<400> SEQUENCE: 4
aggagcagag                                                             10

<210> SEQ ID NO 5
<211> LENGTH: 10
<212> TYPE: DNA
<213> ORGANISM: Homo sapiens

<400> SEQUENCE: 5
ggagcagagg                                                             10

<210> SEQ ID NO 6
<211> LENGTH: 10
<212> TYPE: DNA
<213> ORGANISM: Homo sapiens

<400> SEQUENCE: 6
gagcagaggg                                                             10

<210> SEQ ID NO 7
<211> LENGTH: 10
<212> TYPE: DNA
<213> ORGANISM: Homo sapiens

<400> SEQUENCE: 7
agcagagggg                                                          10

<210> SEQ ID NO 8
<211> LENGTH: 10
<212> TYPE: DNA
<213> ORGANISM: Homo sapiens

<400> SEQUENCE: 8
gggagtccca                                                          10

<210> SEQ ID NO 9
<211> LENGTH: 10
<212> TYPE: DNA
<213> ORGANISM: Homo sapiens

<400> SEQUENCE: 9
ggagtcccag                                                          10

<210> SEQ ID NO 10
<211> LENGTH: 10
<212> TYPE: DNA
<213> ORGANISM: Homo sapiens

<400> SEQUENCE: 10
gagtcccagc                                                          10

<210> SEQ ID NO 11
<211> LENGTH: 10
<212> TYPE: DNA
<213> ORGANISM: Homo sapiens

<400> SEQUENCE: 11
agtcccagcc                                                          10

<210> SEQ ID NO 12
<211> LENGTH: 18
<212> TYPE: DNA
<213> ORGANISM: Homo sapiens

<400> SEQUENCE: 12
caggagcaga ggggtcag                                                 18

<210> SEQ ID NO 13
<211> LENGTH: 19
<212> TYPE: DNA
<213> ORGANISM: Homo sapiens

<400> SEQUENCE: 13
ggagtcccag ccttgggga                                                19

<210> SEQ ID NO 14
<211> LENGTH: 19
<212> TYPE: DNA
<213> ORGANISM: Homo sapiens

<400> SEQUENCE: 14
gggagtccca gccttgttg                                                 19

<210> SEQ ID NO 15
<211> LENGTH: 19
<212> TYPE: DNA
<213> ORGANISM: Homo sapiens

<400> SEQUENCE: 15
atcagtgtcg tcgcggtcg                                                 19

<210> SEQ ID NO 16
<211> LENGTH: 19
<212> TYPE: DNA
<213> ORGANISM: Homo sapiens

<400> SEQUENCE: 16
caggagcaga gacatttac                                                 19

<210> SEQ ID NO 17
<211> LENGTH: 19
<212> TYPE: DNA
<213> ORGANISM: Homo sapiens

<400> SEQUENCE: 17
tggggagtcc caagtaggt                                                 19

<210> SEQ ID NO 18
<211> LENGTH: 19
<212> TYPE: DNA
<213> ORGANISM: Homo sapiens

<400> SEQUENCE: 18
gggagtccca ctgcaagga                                                 19

<210> SEQ ID NO 19
<211> LENGTH: 19
<212> TYPE: DNA
<213> ORGANISM: Homo sapiens

<400> SEQUENCE: 19
ctccccagac ctgcaagga                                                 19

<210> SEQ ID NO 20
<211> LENGTH: 10
<212> TYPE: DNA
<213> ORGANISM: Homo sapiens

<400> SEQUENCE: 20
atcagtgtcg                                                           10

<210> SEQ ID NO 21
<211> LENGTH: 10
<212> TYPE: DNA
<213> ORGANISM: Homo sapiens

<400> SEQUENCE: 21
ggagcagaga                                                           10

<210> SEQ ID NO 22
<211> LENGTH: 10
<212> TYPE: DNA
<213> ORGANISM: Homo sapiens

<400> SEQUENCE: 22

```
tggggagtcc                                                          10

<210> SEQ ID NO 23
<211> LENGTH: 10
<212> TYPE: DNA
<213> ORGANISM: Homo sapiens

<400> SEQUENCE: 23
ctccccagac                                                          10

<210> SEQ ID NO 24
<211> LENGTH: 10
<212> TYPE: DNA
<213> ORGANISM: Homo sapiens

<400> SEQUENCE: 24
gagtcccact                                                          10

<210> SEQ ID NO 25
<211> LENGTH: 10
<212> TYPE: DNA
<213> ORGANISM: Homo sapiens

<400> SEQUENCE: 25
ccccagacct                                                          10
```

|---|---|---|---|---|---|

SYSTEMS AND METHODS FOR DETERMINING THE IDENTITY OF ALLELES FROM GENOMIC SEQUENCING DATA

RELATED APPLICATIONS

This application claims priority to U.S. Provisional Patent Application 62/369,809 filed Aug. 2, 2016. The entire contents of U.S. Provisional Patent Application 62/369,809 is incorporated by reference in its entirety herein.

REFERENCE TO A "SEQUENCE LISTING" SUBMITTED AS ASCII TEXT FILES VIA EFS-WEB

The Sequence Listing written in file 101146-1056829-028US1_SequenceListing.txt created on Sep. 14, 2017, 4,741 bytes, machine format IBM-PC, MS-Windows operating system, in accordance with 37 C.F.R. §§ 1.821- to 1.825, is hereby incorporated by reference in its entirety for all purposes.

FIELD OF THE INVENTION

The present invention relates to gene typing, gene mapping, and mutation detection in samples using genomic sequencing data, and in particular to systems and methods for determining the identity of alleles from genomic sequencing data via pseudoalignments.

BACKGROUND

An allele is one of a number of alternative forms of the same gene or same genetic locus. In some instances different alleles can result in different observable phenotypic traits such as eye color. In other instances different alleles allow for a species to fine tune and evolve various systems such as the immune system. For example, the human leukocyte antigen (HLA) genes are the human version of the major histocompatibility complex (MHC), a gene family that occurs in many species. In humans, the MHC complex consists of more than 200 genes located close together on chromosome six and helps the immune system distinguish the body's own proteins from proteins made by foreign invaders such as viruses and bacteria. The HLA genes have many possible alleles (highly polymorphic), allowing each person's immune system to react to a wide range of foreign invaders. Some HLA genes have hundreds of identified alleles, each of which is given a particular number (such as HLA-B27). In organ transplantation such as haematopoietic stem cell transplantation, matching for HLA alleles between patients and their potential donors is important for success of the transplantation. Moreover, the MHC complex has been associated with more diseases (mainly autoimmune and infectious) than any other region of the genome. For example, the HLA-B27 allele increases the risk of developing an inflammatory joint disease called ankylosing spondylitis. Many other disorders involving abnormal immune function and some forms of cancer have also been associated with specific HLA alleles. Thus, identifying certain HLA alleles in a patient sample is important for disease diagnosis.

In order to improve upon conventional organ transplantation and disease diagnostic techniques, a primary goal for researchers has been to determine which of the thousands of possible known HLA alleles are present in a DNA or RNA sample. Early HLA typing and studies of MHC disease associations relied on laborious serological typing that used sera from patients and monoclonal antibody assays. DNA typing took over from serology, and until recently most clinical HLA typing, to four digits, had been based on polymerase chain reaction (PCR). Single Nucleotide Polymorphism (SNP) typing has been introduced to replace classical HLA typing; however, SNP typing also has limitations. For example, there are a number of ways in which conventional SNP typing falls short for HLA typing, including: (i) many HLA alleles are rare, so combinations of common SNPs do not provide sufficient resolution; (ii) some HLA alleles are embedded in different haplotypes; (iii) the sheer number of alleles calls for typing a large number of SNP tags; and (iv) SNP tags fitted in small, focused studies may not transfer to future projects, particularly with different populations. Accordingly, the need exists for improved techniques for high precision polymorphic allele typing from genomic sequencing data.

BRIEF SUMMARY

In one embodiment, the invention relates to a method for identifying an allele within a genomic sample. The method includes obtaining, by a computing device, a plurality of paired-end fragments from a genomic sample; extracting, by the computing device, a group of nucleotide substrings from each pair-end fragment; comparing, by the computing device, each nucleotide substring within the group of nucleotide substrings to reference nucleotide substrings within an index that provides a mapping between each reference nucleotide substring and an allele that contains the reference nucleotide substring; identifying, by the computing device, for each nucleotide substring, a subset of alleles that contain the nucleotide sub string based on the comparing and the mapping; identifying, by the computing device, alleles that are present in two or more of the identified subset of alleles; determining, by the computing device, for each identified allele, a probability that the genomic sample comprises the allele based on a number of the plurality of paired-end fragments that include a nucleotide substring from the allele; and identifying, by the computing device, an allele is within the genomic sample when the allele has a greatest determined probability compared to that of the determined probabilities for the identified alleles.

In accordance with some aspects, the nucleotide substrings from each pair-end fragment are independently fixed with a length based on a predetermined number of bases. Optionally, the reference nucleotide substrings within the index are independently fixed with the length based on the predetermined number of bases.

In accordance with some aspects, the method further includes extracting, by the computing device, nucleotide data from a reference data set including a plurality of alleles. The nucleotide data includes the reference nucleotide substrings contained within the alleles. The method may further include generating, by the computing device, the index based on the nucleotide data and the alleles such that the index provides the mapping between each reference nucleotide substring and the allele that contains the reference nucleotide substring. Optionally, the extracting the group of nucleotide substrings from each pair-end fragment includes extracting the nucleotide substrings by sliding sequentially along each pair-end fragment a predetermined number of bases.

In accordance with other aspects, the method further includes obtaining, by the computing device, a subsample of the paired-end fragments from the plurality of paired-end fragments; executing, by the computing device, the instructions stored on the non-transitory machine readable storage medium to perform: the extracting, the comparing, the identifying the subset of alleles, the identifying the alleles, the determining the probability, and the identifying the allele within the genomic sample, a predetermined number of times on the subsample of the paired-end fragments; determining, by the computing device, a number of times that the executing the instructions results in the allele being identified within the genomic sample using the subsample of the paired-end fragments; and providing, by the computing device, a confidence that the allele is within the genomic sample based on the determined number of times that the allele is identified within the genomic sample.

In another embodiment, the invention relates to a non-transitory machine readable storage medium having instructions stored thereon that when executed by one or more processors cause the one or more processors to perform a method. The method includes obtaining a plurality of paired-end fragments from a genomic sample; extracting a group of nucleotide substrings from each pair-end fragment; comparing each nucleotide substring within the group of nucleotide substrings to reference nucleotide substrings within an index that provides a mapping between each reference nucleotide substring and an allele that contains the reference nucleotide substring; identifying, for each nucleotide substring, a subset of alleles that contain the nucleotide substring based on the comparing and the mapping; identifying alleles that are present in two or more of the identified subset of alleles; determining, for each identified allele, a probability that the genomic sample comprises the allele based on a number of the plurality of paired-end fragments that include a nucleotide substring from the allele; and identifying an allele is within the genomic sample when the allele has a greatest determined probability compared to that of the determined probabilities for the identified alleles.

In accordance with some aspects, the nucleotide substrings from each pair-end fragment are independently fixed with a length based on a predetermined number of bases. Optionally, the reference nucleotide substrings within the index are independently fixed with the length based on the predetermined number of bases.

In accordance with some aspects, the method further includes extracting nucleotide data from a reference data set including a plurality of alleles. The nucleotide data includes the reference nucleotide substrings contained within the alleles. The method may further include generating the index based on the nucleotide data and the alleles such that the index provides the mapping between each reference nucleotide substring and the allele that contains the reference nucleotide substring. Optionally, the extracting the group of nucleotide substrings from each pair-end fragment includes extracting the nucleotide substrings by sliding sequentially along each pair-end fragment a predetermined number of bases.

In accordance with other aspects, the method further includes obtaining a subsample of the paired-end fragments from the plurality of paired-end fragments; executing the instructions stored on the non-transitory machine readable storage medium to perform: the extracting, the comparing, the identifying the subset of alleles, the identifying the alleles, the determining the probability, and the identifying the allele within the genomic sample, a predetermined number of times on the subsample of the paired-end fragments; determining a number of times that the executing the instructions results in the allele being identified within the genomic sample using the subsample of the paired-end fragments; and providing a confidence that the allele is within the genomic sample based on the determined number of times that the allele is identified within the genomic sample.

In another embodiment, the invention relates to a method for identifying an allele within a genomic sample. The method includes obtaining, by a computing device, a paired-end fragment from the genomic sample; determining, by the computing device, a first nucleotide substring from a first end of the paired-end fragment matches a nucleotide substring within an index that provides a mapping between the nucleotide substring and an allele that contains the nucleotide substring; determining, by the computing device, a second nucleotide substring from a second end of the paired-end fragment matches another nucleotide substring within the index that provides a mapping between the another nucleotide substring and an allele that contains the another nucleotide substring; determining, by the computing device, an intersection between the nucleotide substring and the another nucleotide substring exists, when the allele that contains the nucleotide substring is the same allele that contains the another nucleotide substring; and determining, by the computing device, a probability that the paired end fragment is an observation of the allele that contains the nucleotide substring and the another nucleotide substring based on the existence of the intersection.

In accordance with some aspects, the first nucleotide string and the second nucleotide string are independently fixed with a length based on a predetermined number of bases. Optionally, the nucleotide substring and the another nucleotide substring within the index are independently fixed with the length based on the predetermined number of bases.

In accordance with other aspects, the index comprises a plurality of nucleotide substrings of alleles from at least one of: type I, II and III human leukocyte antigen gene (HLA), Ig lambda chain constant region (IGLC), Ig kappa chain variable region (IGKV), T-cell receptor gamma chain variable, joining and constant regions (TRGV, TRGJ, and TRGC), killer-cell IG-like receptor (KIR), and natural killer gene complex.

In accordance with some aspects, the method further includes identifying, by the computing device, the allele is within the genomic sample based on the determined probability.

In another embodiment, the invention relates to a method that includes extracting, by a computing device, nucleotide data from a reference data set including a plurality of genetic sequences, wherein the nucleotide data includes reference nucleotide substrings of length k contained within the plurality of genetic sequences; generating, by the computing device, a k-mer table based on the nucleotide data and the plurality of genetic sequences such that the k-mer table provides a mapping between each reference nucleotide substring and each genetic sequence from the plurality of genetic sequences that contains the reference nucleotide substring; generating, by the computing device, a set of sequence reads from a genomic sample, wherein the sequence reads are grouped by paired-end fragments; comparing, by the computing device, a first nucleotide substring of the length k from a first end of a paired-end fragment to the reference nucleotide substrings within the k-mer table; determining, by the computing device, whether the first nucleotide substring matches one or more of the reference nucleotide substrings within the k-mer table; comparing, by the computing device, a second nucleotide substring of the length k from a second end of the paired-end fragment to the reference nucleotide substrings within the k-mer table; determining, by the computing device, whether the second nucleotide substring matches one or more of the reference nucleotide substrings within the k-mer table; determining, by the computing device, whether an intersection between the reference nucleotide substrings exists, when the first nucleotide substring matches a reference nucleotide substring within the k-mer table and the second nucleotide substring matches the same reference nucleotide substring within the k-mer table; and determining, by the computing device, that the paired-end fragment is a possible observation of a genetic sequence from the plurality of genetic sequences based on the mapping in the k-mer table, when the intersection between the reference nucleotide substrings exists.

In accordance with some aspects, each genetic sequence from the plurality of genetic sequences is an allele. Optionally, the allele is at least one of: type I, II and III human leukocyte antigen gene (HLA), Ig lambda chain constant region (IGLC), Ig kappa chain variable region (IGKV), T-cell receptor gamma chain variable, joining and constant regions (TRGV, TRGJ, and TRGC), killer-cell IG-like receptor (KIR), and natural killer gene complex.

BRIEF DESCRIPTION OF THE DRAWINGS

The present invention will be better understood in view of the following non-limiting figures, in which.

DETAILED DESCRIPTION

I. Introduction

In various embodiments, the present invention is directed to a method for identifying an allele within a genomic sample. A problem associated with current next-generation techniques for identifying an allele within a genomic sample, however, is the reliance of these techniques on either fully aligning the sample sequencing reads to the genome/transcriptome or performing a full de-novo assembly of those sequencing reads. These approaches are both too slow and too specific to a given data type. Also, most conventional genotyping kits for this type of application use a de-novo assembly of sequencing reads from DNA only.

To address these problems, the present invention is directed to systems and methods that implement an associative assembly procedure employing an index of a reference data set of known allele types such as the immune polymorphism database. For example, one illustrative embodiment of the present disclosure comprises grouping a set of sequencing reads from a genomic sample by paired-end fragment. In some aspects, the paired-end fragment is the fundamental observation that is being counted and not the individual sequence reads. Thereafter, each paired-end read fragment is looked at independently, and overlapping nucleotide substrings of length k (e.g., k-mers) are extracted from each paired-end read fragment by sliding sequentially along the sequencing read. Each k-mer is then looked up in the index of the reference data set of known allele types. Each allele type that is identified from the index is grouped, and an intersection of the group of all such alleles is determined. Advantageously, this procedure can be extremely quick and provides an approximation or pseudo-alignment of each paired-end fragment's compatible alleles without the need for a slow genome alignment or assembly step. The pseudoalignments may be analyzed in a subsequent step to provide the most likely identification of an allele within the genomic sample from the paired-end fragment data. Advantageously, this approach provides a probabilistic estimate associated with each genotype. This estimate can then be used in downstream analysis to more accurately capture the uncertainty associated with each genotype.

While some embodiments are disclosed herein with respect to identifying an HLA allele from DNA sequencing data, this is not intended to be restrictive. In addition to HLA alleles, the teachings disclosed herein can also be applied to other alleles within other regions of a genome. For example, the alleles could be identified for regions or complexes including the Ig lambda chain constant region (IGLC), Ig kappa chain variable region (IGKV), T-cell receptor gamma chain variable, joining and constant regions (TRGV, TRGJ, and TRGC), killer-cell IG-like receptor (KIR), and natural killer gene complex. Likewise, the sequencing data is not restricted to being obtained from DNA. For example, the sequencing data could be obtained from other polymeric material such as RNA. In the instance of RNA, an index of the reference data set could be generated for the human transcriptome where the identifying names are gene transcript names instead of allele names, and their genetic sequence is the coding sequence of the transcript.

II. Techniques for Identifying an Allele within a Genomic Sample

Figure 1:
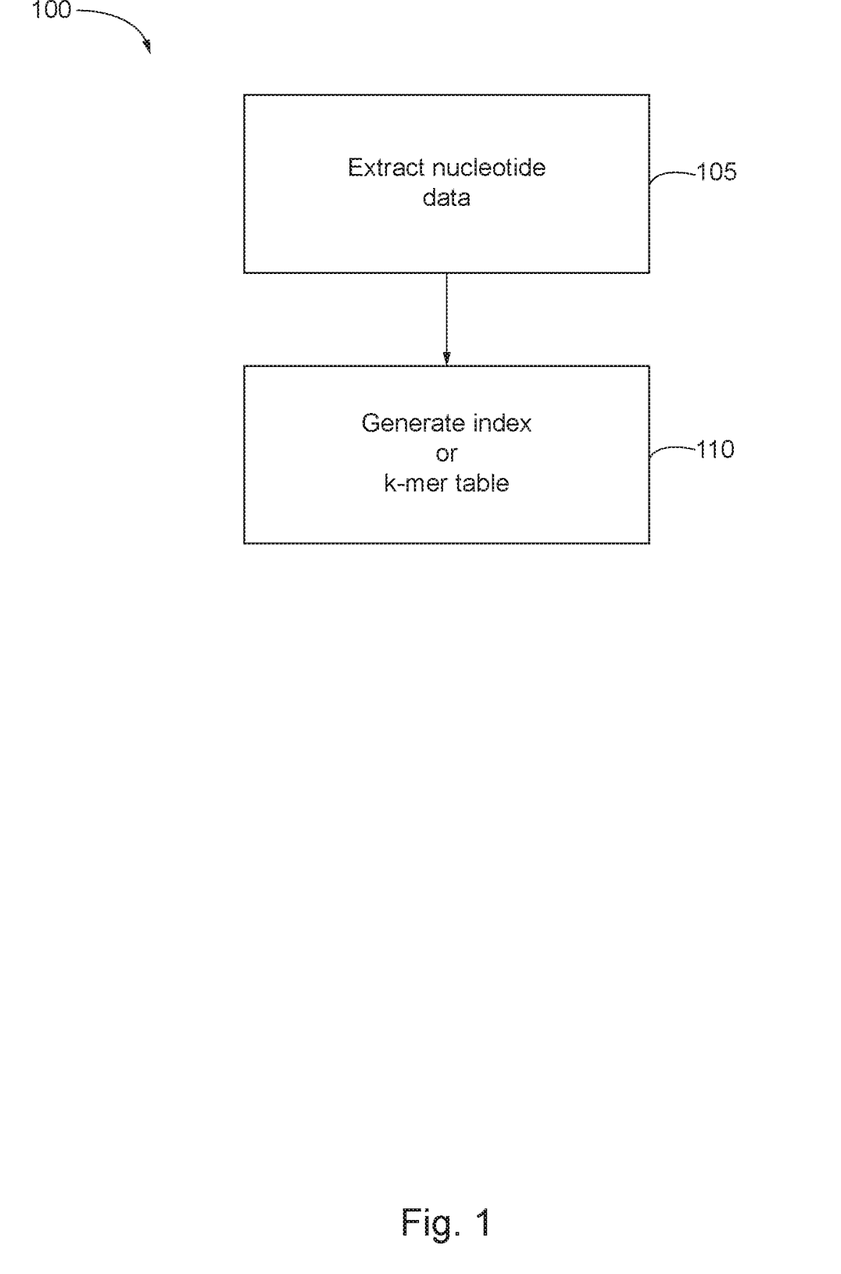
FIG. 1 shows an exemplary flow for indexing a reference data set in accordance with some aspects of the invention.
Figure 2:
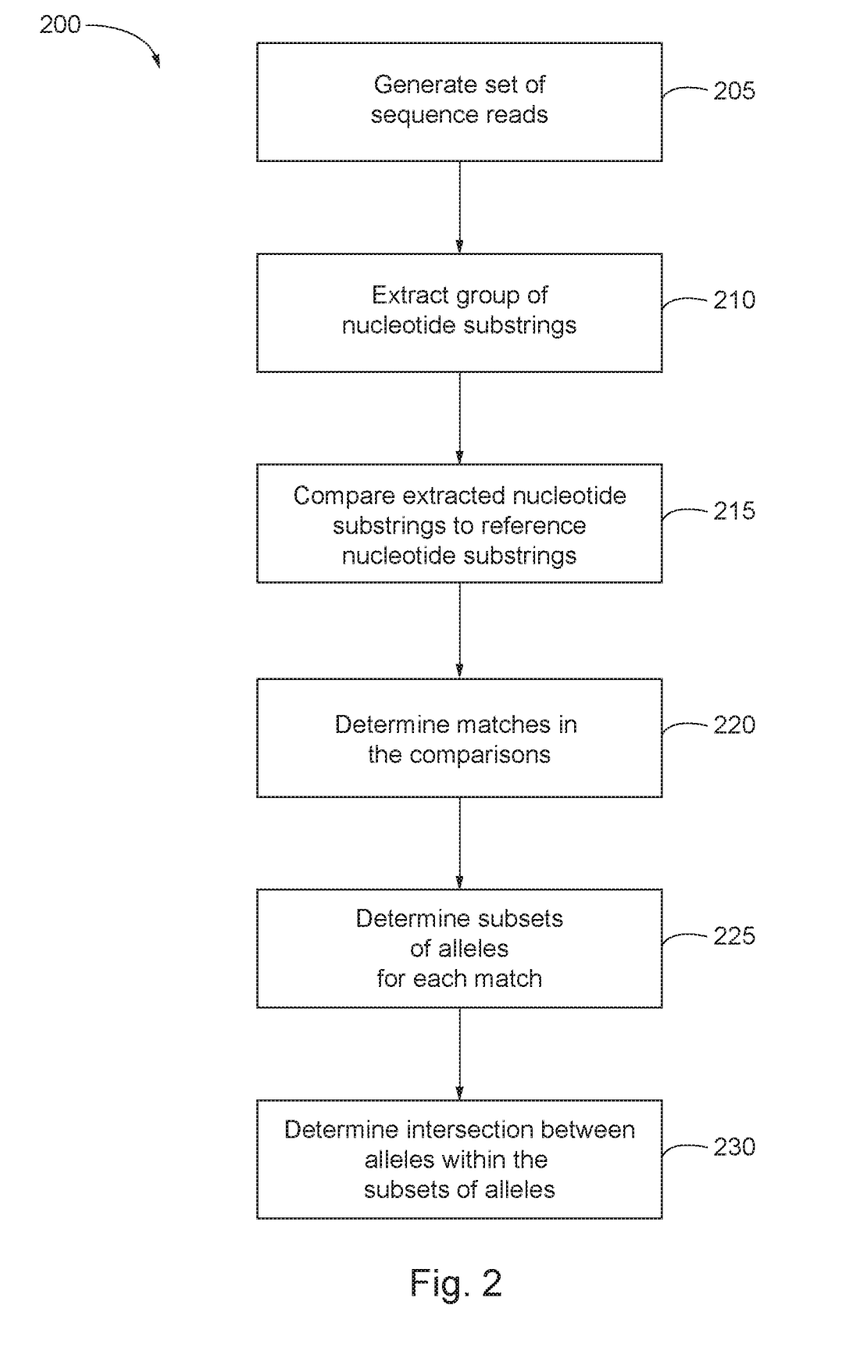
FIG. 2 shows an exemplary flow for identifying an allele within a genomic sample in accordance with some aspects of the invention.
Figure 4:
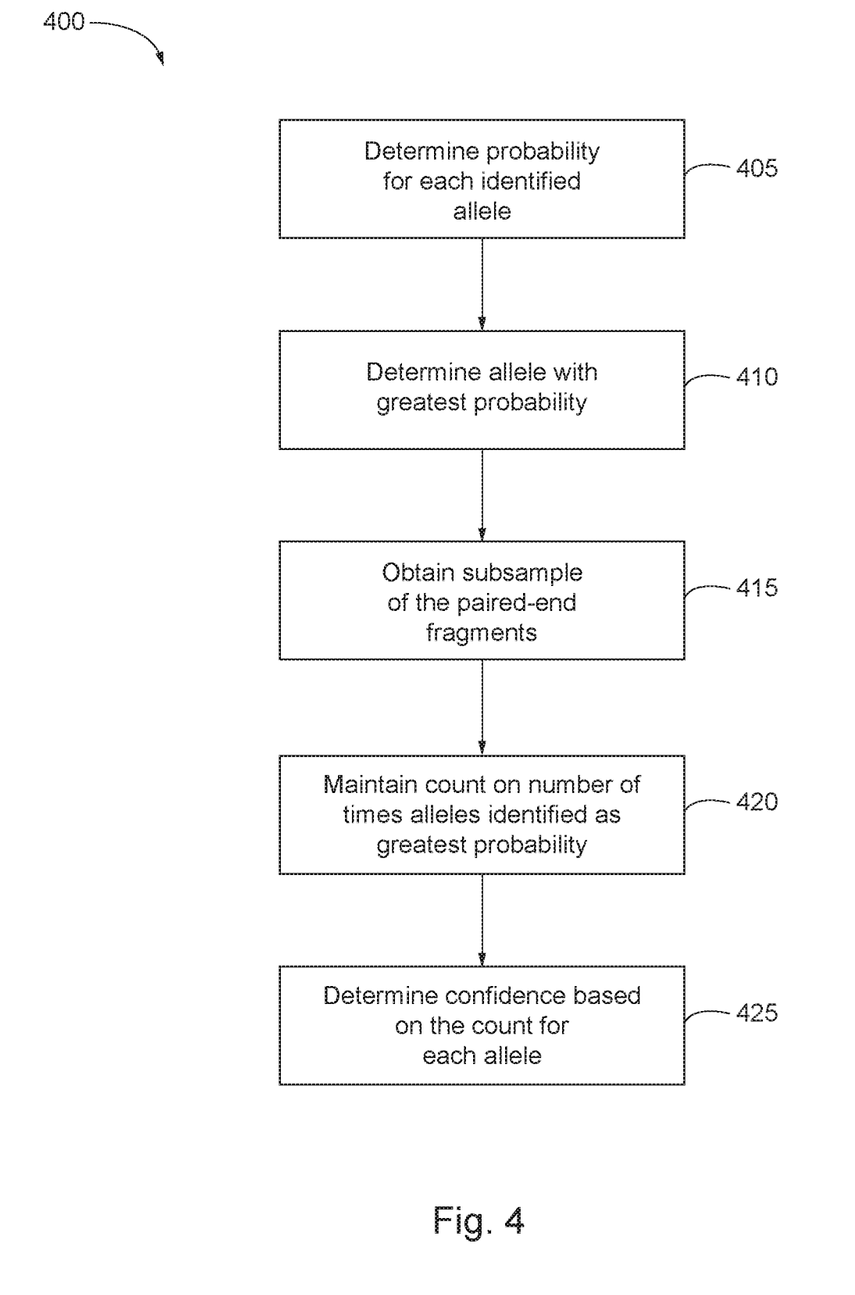
FIG. 4 shows an exemplary flow for identifying probability and confidence of an observation of one or more alleles in accordance with some aspects of the invention.

FIGS. 1, 2, and 4 depict simplified flowcharts depicting processing performed for identifying an allele within a genomic sample according to embodiments of the present invention. The steps of FIGS. 1, 2, and 4 may be implemented in the system environment of FIG. 6, for example. As noted herein, the flowcharts of FIGS. 1, 2, and 4 illustrate the architecture, functionality, and operation of possible implementations of systems, methods, and computer program products according to various embodiments of the present invention. In this regard, each block in the flowchart or block diagrams may represent a module, segment, or portion of code, which comprises one or more executable instructions for implementing the specified logical functions. It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combination of blocks in the block diagrams and/or flowchart illustration, can be implemented by special purpose hardware-based systems that perform the specified functions or acts, or combinations of special purpose hardware and computer instructions.

FIG. 1 depicts a simplified flowchart 100 illustrating a process for indexing a reference data set of known genetic sequences. At step 105, nucleotide data is extracted from a reference data set including a plurality of genetic sequences. In some embodiments, extracting the nucleotide data includes obtaining the plurality of genetic sequences from the reference data set (e.g., downloading the genetic sequences using a universal resource locator (URL) from an online reference data set), and pulling the nucleotide data from the genetic sequences. In alternative embodiments, extracting the nucleotide data includes pulling the nucleotide data directly from the genetic sequences in the reference data set.

Each genetic sequence may be an allele that has been identified within one or more regions of a genome. For example, the alleles may be from at least one of: type I, II and III human leukocyte antigen gene (HLA), Ig lambda chain constant region (IGLC), Ig kappa chain variable region (IGKV), T-cell receptor gamma chain variable, joining and constant regions (TRGV, TRGJ, and TRGC), killer-cell IG-like receptor (KIR), and natural killer gene complex. The reference data set may be a publicly or privately available database comprising known alleles (e.g., HLA alleles) linked together with their canonical allele names. For example, the reference data set may be the ImMuno-GeneTics (IMGT) HLA type database. The nucleotide data may include reference nucleotide substrings of length k contained within the plurality of genetic sequences. For example, the pulling the nucleotide data from the genetic sequences may include using program instructions (e.g., for (int i=0; i<readBases.length( )-kmer+1; i+=5) {// subset of the read returnList.add(readBases.substring(i, i+kmer))) to start at a predetermined base within each genetic sequence string (e.g., the first base), cycle over the genetic sequence string length by a predetermined number (i.e., sliding by one), and extract each reference nucleotide substring of length k based on a predetermined number of bases.

As an example, one can access the file corresponding to HLA-A alleles using: >wget ftp://ftp.ebi.ac.uk/pub/data-bases/ipd/imgt/hla/fasta/A_nuc.fasta from the IMGT HLA type database. This example will be referenced through-out this disclosure and is not intended to limit or define the scope of this disclosure, but rather to provide an illustrative example to aid in the understanding of processes described herein.

In total the IMGT HLA type database contains 14,015 named alleles with their genetic sequence of the form:

>HLA:HLA00001 A*01:01:01:01 3503 bp
(SEQ ID NO: 1)
CAGGAGCAGAGGGGTCAGGGCGAAGTCCCAGGGCCCCAGGCGTGGCTCT

CAGGGTCTCAGGCCCCGAAGGCGGTGTATGGATTGGGGAGTCCCAGCCT

TGGGGATTCCCCAACTCCGCAGTTTCTTTTCTCCCTCTCCCAACCTACG

TAGGGTCCTTCATCCTGGATACTCACGACGCGGACCCAGTTCTCACTCC

CATTGGGTGTCGGGTTTCCAGAGAAGCCAATCAGTGTCGTCGCGGTCGC

TGTTCTAAAGTCCGCACGCACCCACCGGGACTCAGATTCTCCCCAGACG

CCGAGG

. . .etc. . .

>HLA:HLA00004 A*01:04N 3136 bp
(SEQ ID NO: 2)
GGGAGTCCCAGCCTTGGGGATTCCCCAACTCCGCAGTTTCTTTTCTCCC

TCTCCCAACCTACGTAGGGTCCTTCATCCTGGATACTCACGACGCGGAC

CCAGTTCTCACTCCCATTGGGTGTCGGGTTTCCAGAGAAGCCAATCAGT

GTCGTCGCGGTCGCTGTTCTAAAGTCCGCACGCACCCACCGGGACTCAG

ATTCTCCCCAGACGCCGAGGATGGCCGTCATGGCGCCCCGAACCCTCCT

CCTGCTACTCTCGGGGGCCCTGGCCCTGACCCAGACCTGGGCGGGTGAG

TGCGGGGTCGGGAGGGAAACCGCCTCTGCGGGGAGAAGCAAGGGGCCCT

CCTGGCGGGGCGCAGG

. . .etc. . .

The possible k-mers (nucleotide substrings of length k) of the genetic sequences corresponding to the HLA-A alleles may be determined by starting at the first base in each allele and cycling over the string length by one and taking out each substring of length k. For example, starting at the first base with k=10 and the two alleles from above (HLA:HLA00001 A*01:01:01:01 3503 bp and HLA:HLA00004 A*01:04N 3136 bp), the possible k-mers pulled from this reference data set would include:
CAGGAGCAGA (SEQ ID NO: 3)
AGGAGCAGAG (SEQ ID NO: 4)
GGAGCAGAGG (SEQ ID NO: 5)
GAGCAGAGGG (SEQ ID NO: 6)
AGCAGAGGGG (SEQ ID NO: 7)
. . . etc. . . .
GGGAGTCCCA (SEQ ID NO: 8)
GGAGTCCCAG (SEQ ID NO: 9)
GAGTCCCAGC (SEQ ID NO: 10)
AGTCCCAGCC (SEQ ID NO: 11)
. . . etc. . . . .

At step 110, an index or k-mer table based on the nucleotide data and the plurality of genetic sequences is generated such that the k-mer table provides a mapping between each reference nucleotide substring and each genetic sequence from the plurality of genetic sequences that contains the reference nucleotide substring. In some embodiments, generating the index or k-mer table includes exhaustively identifying, for each nucleotide substring of length k, the one or more alleles that include the nucleotide substring of length k, and mapping the nucleotide substring of length k to each of the one or more alleles that include the nucleotide substring of length k. The mapping may include associating the nucleotide substrings of length k with the canonical allele name (e.g., a four digit allele name) of each of the one or more alleles that include the nucleotide substrings of length k.

Continuing with the example above, an index or k-mer table may be generated that includes the following mappings:
CAGGAGCAGA (SEQ ID NO:3)→{A* 01:01}
AGGAGCAGAG (SEQ ID NO:4)→{A* 01:01}
GGAGCAGAGG (SEQ ID NO:5)→{A* 01:01}
GAGCAGAGGG (SEQ ID NO:6)→{A* 01:01}
AGCAGAGGGG (SEQ ID NO:7)→{A* 01:01}
. . . etc. . . .
GGGAGTCCCA (SEQ ID NO:8)→{A* 01:01, A* 01:04N}
GGAGTCCCAG (SEQ ID NO:9)→{A* 01:01, A* 01:04N}
GAGTCCCAGC (SEQ ID NO:10)→{A* 01:01, A* 01:04N}
AGTCCCAGCC (SEQ ID NO:11)→{A* 01:01, A* 01:04N}
. . . etc. . . . .

FIG. 2 depicts a simplified flowchart 200 illustrating a process for identifying an allele within a genomic sample. At step 205, a set of sequence reads from a genomic sample is generated. In some embodiments, generating the sequence reads from a genomic sample such as a biological patient sample containing genomic material includes using any method or technology to determine the order of nucleobases (e.g., adenine, guanine, cytosine, and thymine) in a strand of polymeric material such as DNA or RNA. For example, Illumina® next-generation sequencing (NGS) technology uses clonal amplification and sequencing by synthesis (SBS) chemistry to enable the sequencing of nucleobases. The technology simultaneously identifies nucleobases while incorporating them into a nucleic acid chain. Each nucleobase emits a unique fluorescent signal as it is added to the growing strand, which is used to determine the order of nucleobases in a strand of polymeric material from a genomic sample.

In certain embodiments, a paired-end fragment is determined for each sequence read, and the sequence reads are grouped by paired-end fragment. For example, the genomic sample may be cut into multiple regions, e.g., regions of ~1000 bp, and the order of nucleobases on the forward or positive strand and the reverse or negative strand are determined for each region to generate a set of sequencing reads for the genomic sample. Thereafter, a sequence of nucleobases, for example 100 bp, may be determined for each end of each sequence read. A library may be prepared for the genomic sample that includes information for each sequence read that includes the nucleobase sequence of the first end and the nucleobase sequence of the second end. The sequence reads may be grouped in the library based on the nucleobase sequence of the first end and the nucleobase sequence of the second end (i.e., the paired-end fragment). In some aspects, the paired-end fragment is the fundamental observation that is being counted and not the individual sequence reads.

Continuing with the example above, a set of sequence reads from a genomic sample is generated, a paired-end fragment may be determined for each sequence read, and the sequence reads may be grouped by paired-end fragment, as follows:

```
Group (A1)
Positive Strand (A1)
Paired-End Fragment: CAGGAGCAGAGGGGTCAG ... GGAGTCCCAGCCTTGGGGA
(SEQ ID NO: 12) and (SEQ ID NO: 13), respectively Negative Strand (A1)
Paired-End Fragment: GGGAGTCCCAGCCTTGTTG ... ATCAGTGTCGTCGCGGTCG
(SEQ ID NO: 14) and (SEQ ID NO: 15), respectively Group (A2)
Positive Strand (A2)
Paired-End Fragment: CAGGAGCAGAGACATTTAC ... TGGGGAGTCCCAAGTAGGT
(SEQ ID NO: 16) and (SEQ ID NO: 17), respectively Negative Strand (A2)
Paired-End Fragment: GGGAGTCCCACTGCAAGGA ... CTCCCCAGACCTGCAAGGA
(SEQ ID NO: 18) and (SEQ ID NO: 19), respectively
. . .etc. . .
```

At step 210, a group of nucleotide substrings are extracted from each pair-end fragment. In some embodiments, the nucleotide substrings extracted from each pair-end fragment are independently fixed with a length based on a predetermined number of bases. For example, program instructions (e.g., for (int i=2; i<readBases.length( )-kmer+1; i+=15) {//subset of the read returnList.add(readBases.substring(i, i+kmer))) may be used to start at a predetermined base within each paired-end fragment (e.g., the third base), cycle over the pair-end fragment length by a predetermined number (i.e., sliding by fifteen), and extract each nucleotide substring of length k based on a predetermined number of bases. In certain embodiments, the length k is the same length k of the reference nucleotide substrings extracted from the plurality of genetic sequences described with respect to step 105 of FIG. 1.

Continuing with the example above, nucleotide substrings may be extracted from each pair-end fragment starting at base 1, with a slide of 2, and a k of 10, as follows:

```
Group (A1)
Positive Strand (A1)
Paired-End Fragment:
                                  (SEQ ID NO:12)
CAGGAGCAGAGGGGTCAG ...

(SEQ ID NO:13)
GGAGTCCCAGCCTTGGGGA

Nucleotide Substring (1):
                                  (SEQ ID NO:3)
CAGGAGCAGA ...

(SEQ ID NO:9)
GGAGTCCCAG

Nucleotide Substring (2):
                                  (SEQ ID NO:5)
GGAGCAGAGG ...

(SEQ ID NO:11)
AGTCCCAGCC

Negative Strand (A1)
Paired-End Fragment:
                                  (SEQ ID NO:14)
GGGAGTCCCAGCCTTGTTG ...

(SEQ ID NO:15)
ATCAGTGTCGTCGCGGTCG

Nucleotide Substring (1):
                                  (SEQ ID NO:8)
GGGAGTCCCA ...
```

-continued

ATCAGTGTCG (SEQ ID NO:20)

Nucleotide Substring (2):
GAGTCCCAGC ... (SEQ ID NO:10)

ATCAGTGTCG (SEQ ID NO:20)

Group (A2)
Positive Strand (A2)
Paired-End Fragment:
CAGGAGCAGAGACATTTAC ... (SEQ ID NO:16)

TGGGGAGTCCCAAGTAGGT (SEQ ID NO:17)

Nucleotide Substring (1):
CAGGAGCAGA ... (SEQ ID NO:3)

TGGGGAGTCC (SEQ ID NO:22)

Nucleotide Substring (2):
GGAGCAGAGA ... (SEQ ID NO:21)

GGGAGTCCCA (SEQ ID NO:8)

Negative Strand (A2)
Paired-End Fragment:
GGGAGTCCCACTGCAAGGA ... (SEQ ID NO:18)

CTCCCCAGACCTGCAAGGA (SEQ ID NO:19)

Nucleotide Substring (1):
GGGAGTCCCA ... (SEQ ID NO:8)

CTCCCCAGAC (SEQ ID NO:23)

Nucleotide Substring (2):
GAGTCCCACT ... (SEQ ID NO:24)

CCCCAGACCT (SEQ ID NO:25)

. . .etc. . .

At step 215, each nucleotide substring of the length k within the group of nucleotide substrings extracted from each pair-end fragment is compared to reference nucleotide substrings within an index or k-mer table. For example, a first nucleotide substring of the length k from a first end of a paired-end fragment may be compared to the reference nucleotide substrings within the index or k-mer table, and a second nucleotide substring of the length k from a second end of the paired-end fragment may be compared to the reference nucleotide substrings within the index or k-mer table. This process may continue until all of the nucleotide substrings within each group of nucleotide substrings extracted from each pair-end fragment is compared to each of the reference nucleotide substrings within the index or k-mer table. In some embodiments, the index or k-mer table is generated in accordance with process flow 100 described herein with respect to FIG. 1. In alternative embodiments, the index or k-mer table may be obtained pre-constructed, for example, from a third-party service provider.

At step 220, a determination is made as to whether each nucleotide substring matches one or more of the reference nucleotide substrings within the index or k-mer table based on the comparison. For example, a determination is made as to whether the first nucleotide substring matches one or more of the reference nucleotide substrings within the k-mer table, and a determination is made as to whether the second nucleotide substring matches one or more of the reference nucleotide substrings within the k-mer table. This process may continue until a determination on a match is made for all of the nucleotide substrings within each group of nucleotide substrings extracted from each pair-end fragment.

At step 225, for each nucleotide substring that matches one or more of the reference nucleotide substrings within the index or k-mer table, a subset of alleles that contain the nucleotide substring is identified based on the comparing, determining, and the mapping within the index or k-mer table. For example, since the index or k-mer table provides a mapping between each reference nucleotide substring and an allele that contains the reference nucleotide substring, it is possible to identify for each nucleotide substring that matches one or more of the reference nucleotide substrings within the index or k-mer table, a subset of alleles that contain the nucleotide substring. At step 230, a determination is made as to whether an intersection between the alleles within the subsets of alleles exists. In some embodiments, an intersection is determined or identified when an allele is present in two or more of the identified subset of alleles. When the intersection exists between the alleles within the subsets of alleles, the paired-end fragment is determined to be a possible observation of the allele.

Figure 3:
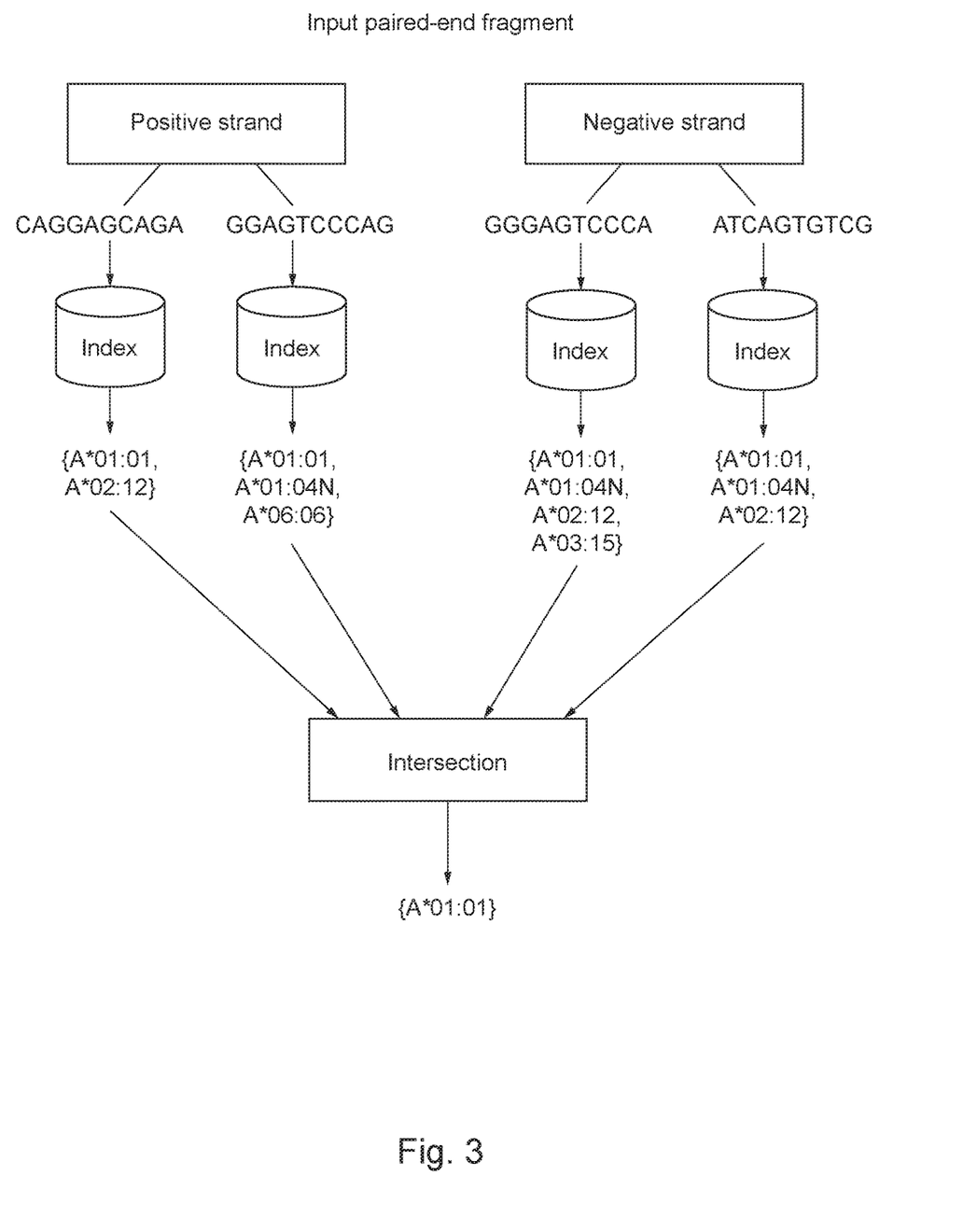
FIG. 3 shows a block diagram for comparing nucleotide substrings (SEQ ID NOS:3, 9, 8, 20, respectively, as presented from left to right) in accordance with some aspects of the invention.

Continuing with the example above and as illustrated in FIG. 3, a determination is made as to whether each nucleotide substring matches one or more of the reference nucleotide substrings within the index or k-mer table, as follows: Positive strand (A1) Nucleotide Substring (1): CAGGAGCAGA (SEQ ID NO:3) GGAGTCCCAG (SEQ ID NO:9) is input into the index or k-mer table and compared to the reference nucleotide substrings within the index or k-mer table. A determination is made as to whether Nucleotide Substring (1): CAGGAGCAGA (SEQ ID NO:3) GGAGTCCCAG (SEQ ID NO:9) matches one or more of the reference nucleotide substrings within the index or k-mer table based on the comparison. From this query a table may be generated that includes the following mappings: CAGGAGCAGA (SEQ ID NO:3)→{A* 01:01, A*02:12}; and GGAGTCCCAG (SEQ ID NO:9)→{A* 01:01, A* 01:04N, A*06:06}.

Subsequently or simultaneously, Negative strand (A1) Nucleotide Substring (1): GGGAGTCCCA (SEQ ID NO:8) . . . ATCAGTGTCG (SEQ ID NO:20) is input into the index or k-mer table and compared to the reference nucleotide substrings within the index or k-mer table. A determination is made as to whether Nucleotide Substring (1): GGGAGTCCCA (SEQ ID NO:8) . . . ATCAGTGTCG (SEQ ID NO:20) matches one or more of the reference nucleotide substrings within the index or k-mer table based on the comparison. From this query a table may be generated that includes the following mappings: GGGAGTCCCA (SEQ ID NO:8)→{A* 01:01, A* 01:04N, A*02:12, A*03:15}; and ATCAGTGTCG (SEQ ID NO:20)→{A* 01:01, A* 01:04N, A* 02:12}.

This process is continued until each nucleotide substring of the length k is compared to the reference nucleotide substrings within the index or k-mer table, and for each nucleotide substring that matches one or more of the reference nucleotide substrings, a subset of alleles that contain the nucleotide substring is identified. Thereafter, a determination is made as to whether an intersection between the alleles within the subsets of alleles exists. For example, A* 01:01 would be identified as an intersection because the paired-ends from Nucleotide Substring (1) from the Positive Strand (A1) and Nucleotide Substring (1) from the Negative strand (A1) all match the allele: A* 01:01.

FIG. 4 depicts a simplified flowchart 400 illustrating a process for identifying an allele with a greatest probability of being present in a genomic sample and providing a confidence that the allele with the greatest probability is within the genomic sample. At step 405, a probability that the genomic sample comprises each allele identified in step 225, described herein with respect to FIG. 2, is determined based on a number of the plurality of paired-end fragments that include a nucleotide substring from the allele. The pseudoalignments between a nucleotide substring of a paired-end fragment and a matching allele are probalistic in a sense that that there are potentially many other alleles that match the nucleotide substring of the paired-end fragment. Consequently, in order to identify an allele with a greatest probability of being present in a genomic sample, at step 410 the probabilities determined for each identified allele in step 405 are compared to one another to identify an allele with the greatest determined probability.

In some embodiments, steps 405 and 410 may be performed using an algorithm such as a standard expectation maximization algorithm to identify the allele with the greatest probability of being present in the genomic sample. This process may work as in the following pseudo code:

```
while (iter<maxIterations && delta>epsilon) {
  // Expectation—calculate the expected value of the fragments given the allele distribution.
    for (int fragment=0; fragment<numFragments; fragment++) {
      double sum=0.0;
      for (int allele=0; allele<numAlleles; allele++) {
        data[fragment][allele]=dataLikelihoods[fragment]
          [allele]*probOfAlleles[allele];
  sum+=data[fragment][allele];
  }
  for (int allele=0; allele<numAlleles; allele++)
    data[fragment][allele]/=sum; // Normalize the distribution.
  }
  }
  // Maximization—maximize the probability of the alleles given the fragments. double sum=0.0;
  for (int allele=0; allele<numAlleles; allele++) {
    updatedProbOfAlleles[allele]=0.0;
    for (int fragment=0; fragment<numFragments; fragment++) {
    updatedProbOfAlleles[allele]+=data[fragment][allele]
      *fragmentSupport[fragment];
    }
    sum+=updatedProbOfAlleles[allele];
  }
  for (int allele=0; allele<numAlleles; allele++) {
    updatedProbOfAlleles[allele]/=sum; // Normalize the distribution.
  }
  // Update delta and allele classes array.
  delta=0.0;
  for (int allele=0; allele<numAlleles; allele++) {
  delta+=Math.abs(probOfAlleles[allele]−updatedProbOfAlleles[allele]); // Used to test for convergence.
  }
  probOfAlleles=updatedProbOfAlleles;
  iter++;
}
return Argmax(probOfAlleles);
```

The pseudo code initializes the distribution of the possible alleles identified in step 225 to be a uniform distribution (equal likelihood of 1/X; were Xis the number of possible alleles). Thereafter, the pseudo code iteratively alternates between: (i) summing over the fragments to compute the likelihood distribution over the possible alleles, and (ii) summing over the possible alleles to compute the maximum likelihood estimate or greatest probability of the allele distribution given the paired-end fragments.

Figure 5:
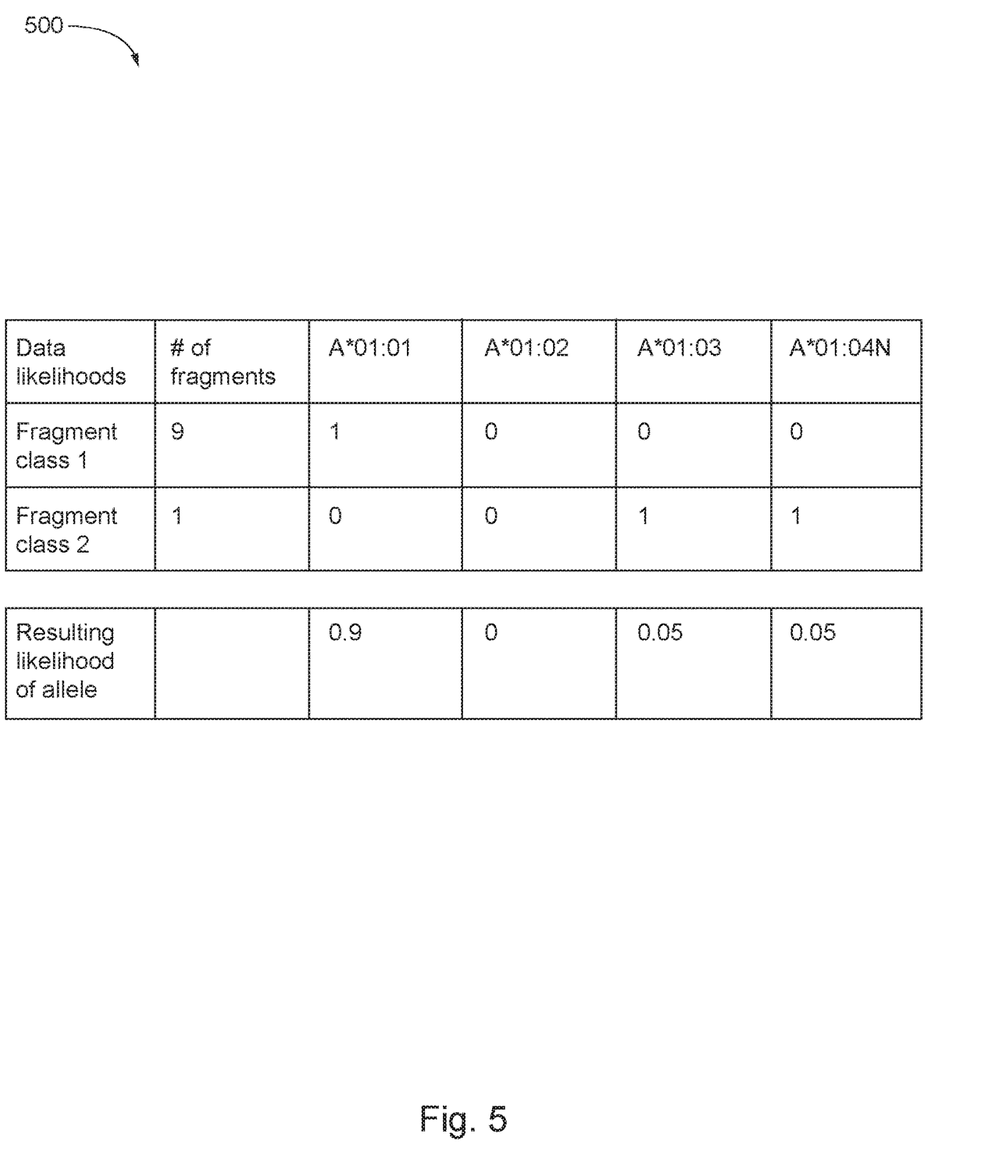
FIG. 5 shows a table of probabilities of alleles being present in a genomic sample in accordance with some aspects of the invention.

Continuing with the example above and as illustrated in FIG. 5, ten paired-end fragments may have been generated from the genomic sample in step 205, described herein with respect to FIG. 2. From those ten, the processes in steps 210-230, described herein with respect to FIG. 2, may have identified nine of the ten paired end fragments as matching or being an observation of allele A* 01:01; and one paired-end fragment matching or being an observation of alleles A*01:03 and A*01:04N, as shown in Table 500 of FIG. 5. The resulting likelihood or probability for: A* 01:01 being the correct observation would be 90%; A*01:03 being the correct observation would be 5%; and A*01:04N being the correct observation would be 5%. Accordingly, the allele with the greatest probability of being present in the genomic sample would be identified as A* 01:01 at 90%.

At step 415, a subsample of the paired-end fragments is obtained from the plurality of paired-end fragments. For example, 20-30% of the paired-end fragments are obtained from the plurality of paired-end fragments generated in step 205, described herein with respect to FIG. 2. At step 420, the subsample of the paired-end fragments are processed a predetermined number of times to identify the alleles with the greatest probability of being present in the genomic sample. For example, 20% of the paired-end fragments are processed using steps 210-230 and 405-410, as described herein with respect to FIGS. 2 and 4, a million times to identify the alleles with the greatest probability of being present in the genomic sample.

At step 420, a count of the number of times that the alleles with the greatest probability of being present in the genomic sample are identified is maintained. In some embodiments, maintaining the count may include determining a number of times that the performance of step 420 results in the alleles being identified within the genomic sample using the subsample of the paired-end fragments. In alternative embodiments, determining a number of times that the alleles are identified within the genomic sample using the subsample of the paired-end fragments.

At step 425, a confidence that the allele is within the genomic sample is provided based on the determined number of times that each allele is identified within the genomic sample. For example, the confidence may be a probability (e.g., N/1,000,000; where N is the number of times that the performance of step 420 results in the alleles being identified within the genomic sample or a number of times that the alleles are identified within the genomic sample). In other words, if the alleles that are identified using the subsample of the paired-end fragments changes from that of the allele identified as having the greatest probability of being present in the genomic sample determined in steps 405 and 410, the confidence in the allele identified in steps 405 and 410 will be relatively low. Advantageously and in contrast to traditional techniques, the processes and algorithm described herein can be performed millions of times extremely fast, which allows for a confidence to be generated that the allele with the greatest probability of being present in the genomic sample is most likely in the genomic sample.

III. System Environment

Figure 6:
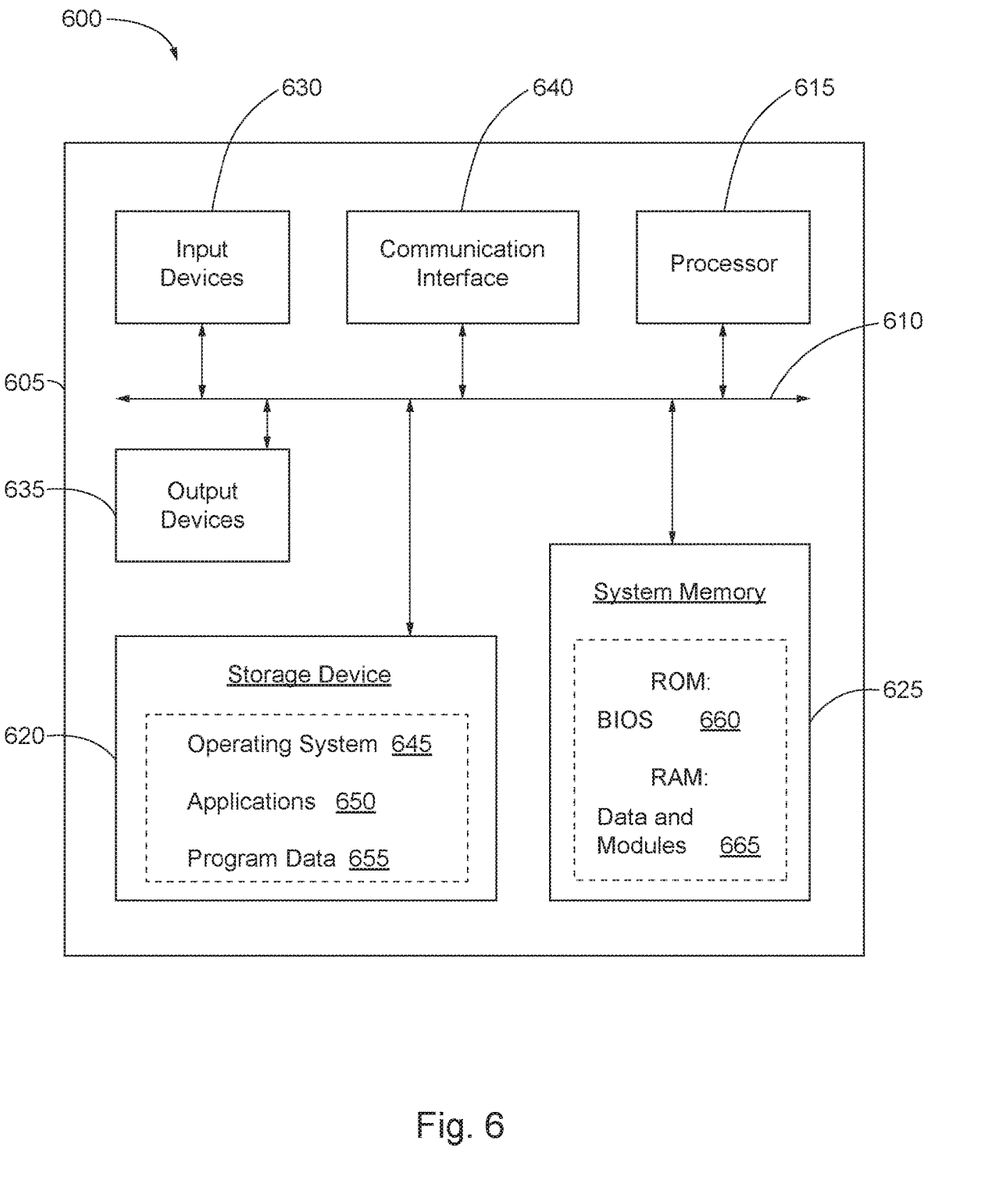
FIG. 6 shows an illustrative architecture of a computing system implemented in accordance with some aspects of the invention.

FIG. 6 is an illustrative architecture of a computing system 600 implemented as some embodiments of the present invention. The computing system 600 is only one example of a suitable computing system and is not intended to suggest any limitation as to the scope of use or functionality of the present invention. Also, computing system 600 should not be interpreted as having any dependency or requirement relating to any one or combination of components illustrated in computing system 600.

As shown in FIG. 6, computing system 600 includes a computing device 605. The computing device 605 can be resident on a network infrastructure such as within a cloud environment, or may be a separate independent computing device (e.g., a computing device of a service provider). The computing device 605 may include a bus 610, processor 615, a storage device 620, a system memory (hardware device) 625, one or more input devices 630, one or more output devices 635, and a communication interface 640.

The bus 610 permits communication among the components of computing device 105. For example, bus 610 may be any of several types of bus structures including a memory bus or memory controller, a peripheral bus, and a local bus using any of a variety of bus architectures to provide one or more wired or wireless communication links or paths for transferring data and/or power to, from, or between various other components of computing device 605.

The processor 615 may be one or more conventional processors, microprocessors, or specialized dedicated processors that include processing circuitry operative to interpret and execute computer readable program instructions, such as program instructions for controlling the operation and performance of one or more of the various other components of computing device 605 for implementing the functionality, steps, and/or performance of the present invention. In certain embodiments, processor 615 interprets and executes the processes, steps, functions, and/or operations of the present invention, which may be operatively implemented by the computer readable program instructions. For example, processor 615 can retrieve, e.g., import and/or otherwise obtain or generate nucleotide data from a reference data set including a plurality of alleles, generate an index based on the nucleotide data, and identify an allele within a genomic sample using the index. In embodiments, the information obtained or generated by the processor 615, e.g., the index, the paired-end fragments, the identification of an allele, etc., can be stored in the storage device 620.

The storage device 620 may include removable/non-removable, volatile/non-volatile computer readable media, such as, but not limited to, non-transitory machine readable storage medium such as magnetic and/or optical recording media and their corresponding drives. The drives and their associated computer readable media provide for storage of computer readable program instructions, data structures, program modules and other data for operation of computing device 605 in accordance with the different aspects of the present invention. In embodiments, storage device 620 may store operating system 645, application programs 650, and program data 655 in accordance with aspects of the present invention.

The system memory 625 may include one or more storage mediums, including for example, non-transitory machine readable storage medium such as flash memory, permanent memory such as read-only memory ("ROM"), semi-permanent memory such as random access memory ("RAM"), any other suitable type of non-transitory storage component, or any combination thereof. In some embodiments, an input/output system 660 (BIOS) including the basic routines that help to transfer information between the various other components of computing device 605, such as during start-up, may be stored in the ROM. Additionally, data and/or program modules 665, such as at least a portion of operating system 645, program modules, application programs 650, and/or program data 655, that are accessible to and/or presently being operated on by processor 615, may be contained in the RAM. In embodiments, the program modules 665 and/or application programs 650 can comprise the index or table, the algorithm such as a standard expectation maximization algorithm to identify the allele with the greatest probability of being present in the genomic sample, and a comparison tool, which provides the instructions for execution of processor 615.

The one or more input devices 630 may include one or more mechanisms that permit an operator to input information to computing device 605, such as, but not limited to, a touch pad, dial, click wheel, scroll wheel, touch screen, one or more buttons (e.g., a keyboard), mouse, game controller, track ball, microphone, camera, proximity sensor, light detector, motion sensors, biometric sensor, and combinations thereof. The one or more output devices 635 may include one or more mechanisms that output information to an operator, such as, but not limited to, audio speakers, headphones, audio line-outs, visual displays, antennas, infrared ports, tactile feedback, printers, or combinations thereof.

The communication interface 640 may include any transceiver-like mechanism (e.g., a network interface, a network adapter, a modem, or combinations thereof) that enables computing device 605 to communicate with remote devices or systems, such as a mobile device or other computing devices such as, for example, a server in a networked environment, e.g., cloud environment. For example, computing device 605 may be connected to remote devices or systems via one or more local area networks (LAN) and/or one or more wide area networks (WAN) using communication interface 640.

As discussed herein, computing system 600 may be configured to identify an allele within a genomic sample. In particular, computing device 605 may perform tasks (e.g., process, steps, methods and/or functionality) in response to processor 615 executing program instructions contained in non-transitory machine readable storage medium, such as system memory 625. The program instructions may be read into system memory 625 from another computer readable medium (e.g., non-transitory machine readable storage medium), such as data storage device 620, or from another device via the communication interface 640 or server within or outside of a cloud environment. In embodiments, an operator may interact with computing device 605 via the one or more input devices 630 and/or the one or more output devices 635 to facilitate performance of the tasks and/or realize the end results of such tasks in accordance with aspects of the present invention. In additional or alternative embodiments, hardwired circuitry may be used in place of or in combination with the program instructions to implement the tasks, e.g., steps, methods and/or functionality, consistent with the different aspects of the present invention. Thus, the steps, methods and/or functionality disclosed herein can be implemented in any combination of hardware circuitry and software.

While the invention has been described in detail, modifications within the spirit and scope of the invention will be readily apparent to the skilled artisan. It should be understood that aspects of the invention and portions of various embodiments and various features recited above and/or in the appended claims may be combined or interchanged either in whole or in part. In the foregoing descriptions of the various embodiments, those embodiments which refer to another embodiment may be appropriately combined with other embodiments as will be appreciated by the skilled artisan. Furthermore, the skilled artisan will appreciate that the foregoing description is by way of example only, and is not intended to limit the invention.

What is claimed is:

1. A method for identifying an allele within a genomic sample, the method comprising:
   obtaining, by a computing device, a plurality of paired-end fragments from a genomic sample;
   extracting, by the computing device, a group of nucleotide substrings from each pair-end fragment;
   comparing, by the computing device, each nucleotide substring within the group of nucleotide substrings to reference nucleotide substrings within an index that provides a mapping between each reference nucleotide substring and an allele that contains the reference nucleotide substring;
   identifying, by the computing device, for each nucleotide substring, a subset of alleles that contain the nucleotide substring based on the comparing and the mapping;
   identifying, by the computing device, alleles that are present in two or more of the identified subsets of alleles;
   determining, by the computing device, for each identified allele, a probability that the genomic sample comprises the allele based on a number of the plurality of paired-end fragments that include a nucleotide substring from the allele; and
   identifying, by the computing device, an allele is within the genomic sample when the allele has a greatest determined probability compared to that of the determined probabilities for the identified alleles.

2. The method of claim 1, wherein the nucleotide substrings from each pair-end fragment are independently fixed with a length based on a predetermined number of bases.

3. The method of claim 2, wherein the reference nucleotide substrings within the index are independently fixed with the length based on the predetermined number of bases.

4. The method of claim 3, further comprising:
   extracting, by the computing device, nucleotide data from a reference data set including a plurality of alleles, wherein the nucleotide data includes the reference nucleotide substrings contained within the alleles; and
   generating, by the computing device, the index based on the nucleotide data and the alleles such that the index provides the mapping between each reference nucleotide substring and the allele that contains the reference nucleotide substring.

5. The method of claim 3, wherein the extracting the group of nucleotide substrings from each pair-end fragment includes extracting the nucleotide substrings by sliding sequentially along each pair-end fragment a predetermined number of bases.

6. The method of claim 1, further comprising:
   obtaining, by the computing device, a subsample of the paired-end fragments from the plurality of paired-end fragments;
   executing, by the computing device, the instructions stored on the non-transitory machine readable storage medium to perform: the extracting, the comparing, the identifying the subset of alleles, the identifying the alleles, the determining the probability, and the identifying the allele within the genomic sample, a predetermined number of times on the subsample of the paired-end fragments;
   determining, by the computing device, a number of times that the executing the instructions results in the allele being identified within the genomic sample using the subsample of the paired-end fragments; and
   providing, by the computing device, a confidence that the allele is within the genomic sample based on the determined number of times that the allele is identified within the genomic sample.

7. A non-transitory machine readable storage medium having instructions stored thereon that when executed by one or more processors cause the one or more processors to perform a method comprising:

obtaining a plurality of paired-end fragments from a genomic sample;

extracting a group of nucleotide substrings from each pair-end fragment;

comparing each nucleotide substring within the group of nucleotide substrings to reference nucleotide substrings within an index that provides a mapping between each reference nucleotide substring and an allele that contains the reference nucleotide substring;

identifying, for each nucleotide substring, a subset of alleles that contain the nucleotide sub string based on the comparing and the mapping;

identifying alleles that are present in two or more of the identified subset of alleles;

determining, for each identified allele, a probability that the genomic sample comprises the allele based on a number of the plurality of paired-end fragments that include a nucleotide substring from the allele; and identifying an allele is within the genomic sample when the allele has a greatest determined probability compared to that of the determined probabilities for the identified alleles.

8. The non-transitory machine readable storage medium of claim 7, wherein the nucleotide substrings from each pair-end fragment are independently fixed with a length based on a predetermined number of bases.

9. The non-transitory machine readable storage medium of claim 8, wherein the reference nucleotide sub strings within the index are independently fixed with the length based on the predetermined number of bases.

10. The non-transitory machine readable storage medium of claim 9, wherein the method further comprises:

extracting nucleotide data from a reference data set including a plurality of alleles, wherein the nucleotide data includes the reference nucleotide substrings contained within the alleles; and generating the index based on the nucleotide data and the alleles such that the index provides the mapping between each reference nucleotide substring and the allele that contains the reference nucleotide substring.

11. The non-transitory machine readable storage medium of claim 9, wherein the extracting the group of nucleotide substrings from each pair-end fragment includes extracting the nucleotide substrings by sliding sequentially along each pair-end fragment a predetermined number of bases.

12. The non-transitory machine readable storage medium of claim 7, wherein the method further comprises:

obtaining a subsample of the paired-end fragments from the plurality of paired-end fragments;

executing the instructions stored on the non-transitory machine readable storage medium to perform: the extracting, the comparing, the identifying the subset of alleles, the identifying the alleles, the determining the probability, and the identifying the allele within the genomic sample, a predetermined number of times on the subsample of the paired-end fragments;

determining a number of times that the executing the instructions results in the allele being identified within the genomic sample using the subsample of the paired-end fragments; and providing a confidence that the allele is within the genomic sample based on the determined number of times that the allele is identified within the genomic sample.

13. A system comprising:

one or more processors and non-transitory machine readable storage medium;

program instructions to obtain a plurality of paired-end fragments from a genomic sample;

program instructions to extract a group of nucleotide substrings from each pair-end fragment;

program instructions to compare each nucleotide substring within the group of nucleotide substrings to reference nucleotide substrings within an index that provides a mapping between each reference nucleotide substring and an allele that contains the reference nucleotide substring;

program instructions to identify for each nucleotide substring, a subset of alleles that contain the nucleotide substring based on the comparing and the mapping;

program instructions to identify alleles that are present in two or more of the identified subsets of alleles;

program instructions to determine for each identified allele, a probability that the genomic sample comprises the allele based on a number of the plurality of paired-end fragments that include a nucleotide substring from the allele; and program instructions to identify an allele is within the genomic sample when the allele has a greatest determined probability compared to that of the determined probabilities for the identified alleles, wherein the program instructions are stored on the non-transitory machine readable storage medium for execution by the one or more processors.

* * * * *